United States Patent
Feuerlein et al.

(10) Patent No.: US 10,470,738 B2
(45) Date of Patent: Nov. 12, 2019

(54) DEFINING SCANNING PARAMETERS OF A CT SCAN USING EXTERNAL IMAGE CAPTURE

(71) Applicant: Siemens Healthcare GmbH, Erlangen (DE)

(72) Inventors: Ute Feuerlein, Erlangen (DE); Stefan Grosskopf, Nuremberg (DE); Grzegorz Soza, Heroldsberg (DE); Michael Suehling, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 269 days.

(21) Appl. No.: 15/496,196

(22) Filed: Apr. 25, 2017

(65) Prior Publication Data
US 2017/0311921 A1   Nov. 2, 2017

(30) Foreign Application Priority Data
Apr. 29, 2016   (DE) .......................... 10 2016 207 367

(51) Int. Cl.
*A61B 6/00*   (2006.01)
*A61B 6/03*   (2006.01)

(52) U.S. Cl.
CPC .............. *A61B 6/545* (2013.01); *A61B 6/032* (2013.01); *A61B 6/481* (2013.01); *A61B 6/488* (2013.01); *A61B 6/542* (2013.01)

(58) Field of Classification Search
CPC ......... A61B 6/545; A61B 6/481; A61B 6/488; A61B 6/542; A51N 6/032

USPC ...................................................... 378/4–20
See application file for complete search history.

(56) References Cited

U.S. PATENT DOCUMENTS

| | | | |
|---|---|---|---|
| 2014/0355735 A1* | 12/2014 | Choi | A61B 6/544 378/8 |
| 2015/0104092 A1 | 4/2015 | Flohr et al. | |
| 2016/0092078 A1 | 3/2016 | Braun et al. | |

FOREIGN PATENT DOCUMENTS

| | | |
|---|---|---|
| DE | 102013220865 A1 | 4/2015 |
| DE | 102014219667 B3 | 3/2016 |

OTHER PUBLICATIONS

German Office Action for Application No. 102016207367.2 dated Jan. 9, 2017.

* cited by examiner

*Primary Examiner* — Courtney D Thomas
(74) *Attorney, Agent, or Firm* — Harness, Dickey & Pierce, P.L.C.

(57) ABSTRACT

A method for defining scanning parameters of a CT scan of a region of interest of an examination object (O) using a CT system is described. In an embodiment of the method, external image capture of external features of the examination object is carried out using an additional image capture unit. In addition, at least one scanning parameter in the axial direction of the CT system is determined on the basis of the external image capture. Finally, a CT scan is performed using the at least one scanning parameter determined. A CT scan range defining device is additionally described. A computed tomography system is also described.

23 Claims, 3 Drawing Sheets

FIG 3

DEFINING SCANNING PARAMETERS OF A CT SCAN USING EXTERNAL IMAGE CAPTURE

PRIORITY STATEMENT

The present application hereby claims priority under 35 U.S.C. § 119 to German patent application number DE 102016207367.2 filed Apr. 29, 2016, the entire contents of which are hereby incorporated herein by reference.

FIELD

At least one embodiment of the invention generally relates to a method for defining scanning parameters of a CT scan of a region of interest of an examination object using a CT system. At least one embodiment of the invention further generally relates to a CT scanning parameter defining device. At least one embodiment of the invention lastly generally relates to a computed tomography system.

BACKGROUND

Using modern imaging methods, two- or three-dimensional image data is frequently produced which can be used for visualizing an examination object and, in addition, for other applications also.

The imaging methods are often based on the detection of X-radiation, wherein so-called projection measurement data is generated. Projection measurement data can be acquired, for example, using a computed tomography system (CT system). In CT systems, a gantry-mounted combination of X-ray source and oppositely disposed X-ray detector usually revolves around a scanning chamber in which the examination object (which, without limitation of generality, will be referred to as the patient in the following) is positioned. The center of rotation (also termed the "isocenter") coincides with a so-called system axis z. In the course of one or more revolutions, the patient is irradiated with X-radiation from the X-ray source, wherein the X-ray detector opposite is used to acquire projection measurement data or more specifically X-ray projection data.

The X-ray detectors employed in CT imaging usually have a plurality of detection units which are mostly arranged in the form of a regular pixel array. The detection units each generate, for the X-radiation incident on the detection units, a detection signal which is analyzed at particular points in time in respect of intensity and spectral distribution in order to draw conclusions about the examination object and to produce projection measurement data.

For imaging body structures of patients, so-called contrast agents are frequently used. However, before contrast-agent-based medical imaging can commence, it must be ensured that, having been injected into the patient's body, the contrast agent is also in the area of the patient's body that is to be examined.

Often the point in time at which imaging is to commence is simply estimated on the basis of empirical values. However, such an approach is not particularly precise. If the scan start time is set too late, this increases the total length of time for which the contrast agent is in the patient. However, the aim is basically to achieve a maximally short residence time of the contrast agent in the body, as the contrast agent can be harmful to the human body. If imaging is started too early, this may result in poorer image quality. In the worst case scenario, imaging and also the administration of contrast agent will even have to be repeated, which places an additional burden on the patient.

One option for making the spread of the contrast agent in the body visible prior to actual imaging involves carrying out a so-called bolus tracking scan (BT scan for short) which is performed prior to actual imaging. Such a BT scan can be a low-resolution, time-dependent scan, e.g. a CT scan with which a time-density curve of a sub-region of a region of interest is acquired.

Such a sub-region for a BT scan usually encompasses a slice which is formed and also viewed orthogonally to the z-direction, i.e. the direction of the system axis of the imaging system. Specifically in the case of the BT scan, attenuation values are acquired as a function of time and space in a sub-region of the region of interest in which usually an artery is located. If the injected contrast agent now flows through the observed artery, the attenuation values are significantly increased. If a predetermined limit value of the attenuation values is exceeded, e.g. 150 Hounsfield units (HU), this can be interpreted as indicating that the contrast agent is present in sufficient concentration in the region of interest, and the actual imaging examination can commence. For such a bolus scan, the position of a slice to be imaged in the bolus scan must be determined prior to the actual imaging.

In general, for CT image acquisition, an extent of a region to be imaged in the z-direction, also referred to as a scan range in the following, and a width of the region to be imaged which defines the so-called field of view (FoV), and possibly also the position of a slice to be imaged in a bolus scan are determined in advance. For this purpose a so-called topogram is generally obtained. This is a two-dimensional X-ray projection of the patient. On the basis of the topogram, the scan start position, the end position of the scanning process, hereinafter amalgamated as the scan range, and the field of view as well as possibly the positioning of a bolus scan slice are determined by technical personnel or using an automated algorithm.

However, the topogram-based planning of a CT imaging sequence means additional workload. In addition, the patient has to wait for a longer time in the CT system to enable the topogram to be obtained. Moreover, the acquisition of a topogram places an additional radiation load on the patient.

SUMMARY

At least one embodiment of the present invention is, in conjunction with the CT imaging, is directed to a simplified and more effective method for defining scanning parameters of a CT scan.

At least one embodiment of the present invention is directed to a method for defining scanning parameters of a CT scan; at least one embodiment is directed to a CT scanning parameter defining device; and at least one embodiment is directed to a computed tomography system.

In at least one embodiment of the inventive method for defining scanning parameters of a CT scan of a region of interest of a patient using a CT system, external image capture of external features of an examination object is performed using an additional image capture unit. The externally captured image is preferably a 3D image which clearly shows the three-dimensional outlines of the examination object. Alternatively, a 2D image capture unit, e.g. a 2D camera, can be used for producing the externally captured image if, for example, the position of an internal structure only needs to be determined in two dimensions on the basis of the externally captured image, as additional information is available in respect of a position of the structures to be imaged in the third dimension. Said external features include in particular the surface of the examination object and its position and orientation. On the basis of the externally captured image, at least one scanning parameter, e.g. a scan range in the axial direction of the CT system, is determined. In the case of determining a scan range, the position and the length of the scan range of the following CT scan in the z-direction is determined. In addition, a CT scan is carried out using the at least one scanning parameter determined. In this context, a scanning parameter shall be regarded as a CT imaging parameter which is determined or defined depending on individual features of the examination object and/or the type and specification of a CT scan to be performed. Such a scanning parameter or rather the parameter value assigned thereto is usually defined in a scan protocol. Where the determining of a scanning parameter is referred to, unless explicitly stated otherwise, this shall always include the determining of a scanning parameter value assigned to the scanning parameter. The externally captured image first gives information about the outlines of an examination object, in particular of a patient and the position and orientation thereof. From the outlines, certain landmarks, in the case of a patient the position of individual body parts, for example, can be determined which provide points of reference in respect of a body part or organ to be imaged. Thus scanning parameters such as, for example, parameters relating to the region of interest, i.e. the scan range, can be estimated or determined on the basis of information obtained from the externally captured image.

At least one embodiment of the inventive CT scanning parameter defining device for defining scanning parameters of a CT scan of a region of interest of a patient using a CT system has a control unit which is designed to control an external image capture unit for carrying out external image capture of the examination object. Moreover, part of at least one embodiment of the inventive CT scanning parameter defining device is a scanning parameter determining unit for determining at least one scanning parameter or rather a parameter value assigned to the scanning parameter in question on the basis of the externally captured image.

At least one embodiment of the computed tomography system according to the invention comprises a scanning unit for acquiring a region of interest of a patient using X-radiation. The computed tomography system according to at least one embodiment of the invention also has a control device for controlling the scanning unit. In addition, the computed tomography system according to at least one embodiment of the invention also comprises an inventive CT scanning parameter defining device.

At least one embodiment of the invention can be largely implemented in the form of software components. This applies particularly to parts of the control unit and to the scanning parameter determining unit. In principle, however, especially when particularly rapid calculation are involved, some of these components can also be realized in the form of software-supported hardware, e.g. FPGAs or similar. Likewise, any interfaces that may be required between the individual units, e.g. when only data transfer from other software components is involved, can be implemented as software interfaces. However, they can also be implemented as hardware-based interfaces controlled by suitable software.

The advantage of a largely software-based implementation is that, following hardware modification, e.g. by adding a camera and an appropriate interface for controlling the camera, also computed tomography systems previously used can be simply upgraded by a software update in order to operate in the inventive manner. In this respect the object is also achieved by a corresponding computer program product comprising a computer program which can be loaded directly into a storage device of a computed tomography system, having program sections for carrying all the steps of the method according to an embodiment of the invention when the program is run in the computed tomography system.

In particular, at least one embodiment is directed to a computer program product that can be the computer program or have at least one additional component aside from the computer program. For example, the at least one additional component of the computer program product can be selected from the group comprising

- a storage device on which at least part of the computer program is stored,
- a key for authenticating a user of the computer program, wherein the key can be implemented in the form of hardware (e.g. a dongle) and/or software,
- documentation relating to the computer program, in a printed and/or digital version,
- a first additional computer program which together with the computer program constitutes a software package,
- a second additional computer program which is designed to compress and/or decompress the computer program and/or which together with the computer program constitutes an installation package,
- a third additional computer program which is designed to distribute processing steps executed when running the computer program to different processing units of a cloud computing system and/or which together with the computer program constitutes a cloud computing application, and combinations thereof.

For transfer to the computed tomography system and/or for storage on or in the computed tomography system, a computer-readable medium such as a memory stick, a hard disk or other transportable or built-in data medium can be used on which the program sections that can be read and executed by a processor unit of the computed tomography system are stored. For this purpose the processor unit can have e.g. one or more co-operating microprocessors or similar.

The claims and the following description contain in each case particularly advantageous embodiments and further developments of the invention. In particular, the claims of one claim category can also be further developed analogously to the dependent claims of another claim category. In addition, within the scope of the invention, the various features of different example embodiments and claims can also be combined to produce new example embodiments.

BRIEF DESCRIPTION OF THE DRAWINGS

The invention will now be explained again in greater detail using example embodiments and with reference to the accompanying drawings in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment of the inventive method for defining scanning parameters of a CT scan of a region of interest of a patient using a CT system, external image capture of external features of an examination object is performed using an additional image capture unit. The externally captured image is preferably a 3D image which clearly shows the three-dimensional outlines of the examination object. Alternatively, a 2D image capture unit, e.g. a 2D camera, can be used for producing the externally captured image if, for example, the position of an internal structure only needs to be determined in two dimensions on the basis of the externally captured image, as additional information is available in respect of a position of the structures to be imaged in the third dimension. Said external features include in particular the surface of the examination object and its position and orientation. On the basis of the externally captured image, at least one scanning parameter, e.g. a scan range in the axial direction of the CT system, is determined. In the case of determining a scan range, the position and the length of the scan range of the following CT scan in the z-direction is determined. In addition, a CT scan is carried out using the at least one scanning parameter determined. In this context, a scanning parameter shall be regarded as a CT imaging parameter which is determined or defined depending on individual features of the examination object and/or the type and specification of a CT scan to be performed. Such a scanning parameter or rather the parameter value assigned thereto is usually defined in a scan protocol. Where the determining of a scanning parameter is referred to, unless explicitly stated otherwise, this shall always include the determining of a scanning parameter value assigned to the scanning parameter. The externally captured image first gives information about the outlines of an examination object, in particular of a patient and the position and orientation thereof. From the outlines, certain landmarks, in the case of a patient the position of individual body parts, for example, can be determined which provide points of reference in respect of a body part or organ to be imaged. Thus scanning parameters such as, for example, parameters relating to the region of interest, i.e. the scan range, can be estimated or determined on the basis of information obtained from the externally captured image.

At least one embodiment of the inventive method for defining the scanning parameters advantageously obviates the need for a topogram obtained in advance. This simplifies the imaging process, the length of time that a patient has to stay in a CT scanner is reduced, and the patient's radiation load is likewise somewhat reduced due to the elimination of the X-ray based topogram.

At least one embodiment of the inventive CT scanning parameter defining device for defining scanning parameters of a CT scan of a region of interest of a patient using a CT system has a control unit which is designed to control an external image capture unit for carrying out external image capture of the examination object. Moreover, part of at least one embodiment of the inventive CT scanning parameter defining device is a scanning parameter determining unit for determining at least one scanning parameter or rather a parameter value assigned to the scanning parameter in question on the basis of the externally captured image.

At least one embodiment of the computed tomography system according to the invention comprises a scanning unit for acquiring a region of interest of a patient using X-radiation. The computed tomography system according to at least one embodiment of the invention also has a control device for controlling the scanning unit. In addition, the computed tomography system according to at least one embodiment of the invention also comprises an inventive CT scanning parameter defining device.

The advantages of implementing at least one embodiment of the invention in a CT system are that the scanning time of a CT system is relatively short. It is only a few seconds compared to MRT systems, which can take several minutes. This is particularly advantageous for examining emergency patients for which any delay can be life-threatening. In addition, CT systems are more widely used and less expensive than MRT systems.

The basic components of the CT scanning parameter defining device according to at least one embodiment of the inventive CT scanning parameter defining device for defining scanning parameters of a CT scan of a region of interest of a patient using a CT system has a control unit which is designed to control an external image capture unit for carrying out external image capture of the examination object. Moreover, part of at least one embodiment of the inventive CT scanning parameter defining device is a scanning parameter determining unit for determining at least one scanning parameter or rather a parameter value assigned to the scanning parameter in question on the basis of the externally captured image.

At least one embodiment of the computed tomography system according to the invention comprises a scanning unit for acquiring a region of interest of a patient using X-radiation. The computed tomography system according to at least one embodiment of the invention also has a control device for controlling the scanning unit. In addition, the computed tomography system according to at least one embodiment of the invention also comprises an inventive CT scanning parameter defining device.

At least one embodiment of the invention can be largely implemented in the form of software components. This applies particularly to parts of the control unit and to the scanning parameter determining unit. In principle, however, especially when particularly rapid calculation are involved, some of these components can also be realized in the form of software-supported hardware, e.g. FPGAs or similar. Likewise, any interfaces that may be required between the individual units, e.g. when only data transfer from other software components is involved, can be implemented as software interfaces. However, they can also be implemented as hardware-based interfaces controlled by suitable software.

The advantage of a largely software-based implementation is that, following hardware modification, e.g. by adding a camera and an appropriate interface for controlling the camera, also computed tomography systems previously used can be simply upgraded by a software update in order to operate in the inventive manner. In this respect the object is also achieved by a corresponding computer program product comprising a computer program which can be loaded directly into a storage device of a computed tomography system, having program sections for carrying all the steps of the method according to an embodiment of the invention when the program is run in the computed tomography system.

In particular, at least one embodiment is directed to a computer program product that can be the computer program or have at least one additional component aside from the computer program. For example, the at least one additional component of the computer program product can be selected from the group comprising a storage device on which at least part of the computer program is stored, a key for authenticating a user of the computer program, wherein the key can be implemented in the form of hardware (e.g. a dongle) and/or software, documentation relating to the computer program, in a printed and/or digital version, a first additional computer program which together with the computer program constitutes a software package, a second additional computer program which is designed to compress and/or decompress the computer program and/or which together with the computer program constitutes an installation package, a third additional computer program which is designed to distribute processing steps executed when running the computer program to different processing units of a cloud computing system and/or which together with the computer program constitutes a cloud computing application, and combinations thereof.

For transfer to the computed tomography system and/or for storage on or in the computed tomography system, a computer-readable medium such as a memory stick, a hard disk or other transportable or built-in data medium can be used on which the program sections that can be read and executed by a processor unit of the computed tomography system are stored. For this purpose the processor unit can have e.g. one or more co-operating microprocessors or similar.

The claims and the following description contain in each case particularly advantageous embodiments and further developments of the invention. In particular, the claims of one claim category can also be further developed analogously to the dependent claims of another claim category. In addition, within the scope of the invention, the various features of different example embodiments and claims can also be combined to produce new example embodiments.

In one embodiment of the inventive method for defining scanning parameters of a CT scan of a region of interest of an examination object using a CT system, the at least one scanning parameter determined is a parameter of one of the following parameter types:

a position and/or at least one dimension of a scan range running in the axial direction of the CT system, a scanning parameter for modulating the X-ray dose.

Within the scope of this embodiment of the method according to the invention, for the case of determining at least one scanning parameter for a scan range during the step of performing a CT scan, the CT scan is carried out in the scan range determined or defined by the at least one scanning parameter.

In this context, the scan range is to be regarded as a section which is scanned by X-radiation during subsequent CT imaging. As already mentioned, whenever the scan range is referred to in the application, it is the position and extent of the scan range in the z-direction that is meant.

For the case of determining at least one scanning parameter for modulating the X-ray dose, in the step of performing a CT scan the X-ray dose is modulated depending on the at least one scanning parameter determined. In this case, the X-ray density for the automatic modulation of the X-ray dose, for example, is determined from the externally captured images and CT reference image data.

In an embodiment of the method according to the invention for defining scanning parameters of a CT scan of a region of interest of an examination object using a CT system, the field of view is determined on the basis of the external image capture. That is to say, it is particularly the width or more specifically the position and dimensions of the region of interest in the width direction that is determined. In addition, on the basis of the external image capture, a slice of the region of interest can also be determined as the slice for observing a contrast agent bolus. In this context, the region of the examination object from which image data is reconstructed after the CT scan shall be understood as being the region of interest, also termed the field of view. The extent of the field of view in the z-direction usually corresponds to the length of the scan range. However, the field of view may be at variance with the scan range in width or also in the depth direction, but only in that the field of view is a sub-region of the scan range, i.e. of the region scanned during CT imaging. The field of view should be selected such that an organ or body part to be imaged is centered in the field of view, as this is the only way of achieving a sharp CT image of the organ or body part of interest. Such centering is particularly important for cardiac imaging. The externally captured image gives certain points of reference for the position of an organ or body part to be imaged. The field of view can therefore be estimated or determined on the basis of this information obtained from external image capture.

In addition, it is preferable that the at least one scanning parameter and/or the field of view is also determined on the basis of CT reference image data. If CT image data of comparable objects, i.e. patients, is additionally consulted, the position and dimensions of internal structures to imaged using the CT imaging method, particularly organs or other internal body parts, can be inferred from these similarly structured objects. This therefore gives precision to the rough estimation, performed on the basis of an outline scan, of the position and dimension of a structure to be imaged.

With particular preference, for the method according to an embodiment of the invention, the scan range is readjusted during the CT scan on the basis of already acquired CT image data. In this particularly advantageous embodiment, for CT imaging preferably low-resolution provisional image data is obtained virtually in real time on the basis of the X-ray projection scan data acquired during CT scanning. On the basis of this provisional image data of the interior of the examination object, very precise information in respect of the position and dimensions, particularly the start and end, of the internal structures to be imaged can be obtained. From this, for example, an end point for the scanning process can be determined and in this way the scan range or rather the dimensions thereof can be readjusted during the CT imaging process. The estimation of a scan range initially made on the basis of outline imaging of the patient can therefore be made increasingly precise during the CT imaging. Consequently, in this embodiment increased precision for defining a scan range is achieved which in particular protects the patient from excessive X-ray irradiation of sensitive regions and at the same time ensures that the entire diagnostically necessary region is scanned.

The method according to an embodiment of the invention can be carried out particularly simply and conveniently if the CT scan is terminated in a fully automated manner depending on the readjusted scan range. In this variant, the operating personnel do not need to intervene in the CT imaging process in order to terminate it. This reduces operating personnel workload, thereby enabling them to concentrate on monitoring other aspects of the imaging.

In a variant of the method according to an embodiment of the invention, the scanning speed for the CT scan is automatically reduced shortly before reaching the end of the readjusted scan range. This variant may also be regarded as semi-automatic scan range monitoring. During ongoing CT imaging, an imminent end of the scan range is detected in an automated manner and the slowing-down of the CT scan gives the operating personnel the possibility of manually stopping the imaging process in a timely manner on reaching the end of the scan range. The lower scanning speed increases the accuracy for manually stopping the scanning process. The imminent end of the scanning process can be additionally implemented, for example, by displaying an indication in respect of the distance (e.g. in mm) of the current scanning position from a stop position. In addition, the stop position determined and the current scanning position can also be indicated to the operating personnel on a personalized patient avatar or an anatomical pictogram. Moreover, a color scheme or a traffic-signal-like color code can indicate the distance from the stop position. Thus, for example, as the scanning unit nears the end of the scan range, a traffic signal can change from the color green to the color red.

In a particularly preferred variant of the method according to an embodiment of the invention for defining scanning parameters of a CT scan of a region of interest of an examination object using a CT system, the equipment is switched to another CT scanning mode with a lower scanning speed prior to reaching the end of the readjusted scan range. For example, switching takes place from a mode in which scanning is performed using a spiral scan to a mode in which a so-called sequence scan is performed which takes much longer than the first mentioned scanning method and in which a reconstruction method is used which requires no (constant) table advance in the z-direction. Advantageously, however, the largest part of the scanning process can be carried out using the faster spiral scan method, thereby saving time.

The method according to an embodiment of the invention can also be embodied such that the CT reference image data is used according to one of the following procedures, hereinafter referred to as sub-variants, for determining the least one scanning parameter, preferably relating to the scan range:

the CT reference image data is used unchanged, wherein the CT reference image data which best matches the examination object is selected from a database,
the CT reference image data is deformed in order to match it to the image data already acquired by the CT scan,
the CT reference image data is generated using a statistical model on the basis of a large totality of CT reference image data.

In the case of the first sub-variant, only a comparison process and a selection step have to be performed in order to find suitable reference image data for a more precise definition of a scan range. The comparison process comprises, for example, the comparison of volumes obtained on the basis of external image capture with the corresponding volumes in the CT reference data of the database. In addition, further information can also be used for the selection, such as, for example, an assigned scan protocol, the patient's sex, age and weight. In the case of the second sub-variant, deformation of the CT reference image data also takes place in order to match it to the image data already acquired using the CT scan. Here, CT reference image data is registered to the already acquired CT image data in order to match the CT reference image data even more precisely to the shape and size of the actual structures, thereby enabling an even more precise estimation of the position of the internal structures, particularly internal organs and their dimensions, to be performed. Lastly, in the case of the third sub-variant, a wide database is used for the generation of CT reference image data and a statistical model which is based on the wide database is employed in order to select suitable CT reference image data. For example, the statistical model can use additional information available for the patient for the weighting of the CT reference image data of the database in order to perform individual matching to the specific patient on a model basis.

In an advantageous variant of the method according to an embodiment of the invention, the scan range is readjusted on the basis of a machine learning process which is applied to the already recorded CT image data. Such methods can be regression-based, for example. Here the position of an anatomical structure at which the scanning process is to be stopped is determined by a regression method. The determination takes place on the basis of anatomical structures already detected during imaging. For example, for imaging of the lung, the position of the underside of the lung shall be determined by regression. This can take place, for example, on the basis of already scanned anatomical structures, such as the carina or heart, for example.

In a particularly advantageous variant of the method according to an embodiment of the invention, the readjustment of the scan range includes registering the CT reference image data used for preliminary determination of the scan range to the already recorded CT image data. With particular preference for the readjustment, after scanning of one or more new CT image slices, new reference image data as similar as possible to the recorded CT image data is again selected from a database in an automated manner. In this variant, the CT reference image data used for determining or rather rendering more precise the end point position of the scan range is continuously updated during actual CT imaging, so that a reference database matched as precisely as possible to the situation in the scan range is used in order to determine the end point of the scan range.

In a likewise very advantageous embodiment of the method according to the invention, on completion of the recording of the CT image data, the field of view is readjusted on the basis of the recorded CT image data. That is to say, the image region to be reconstructed or rather its dimension and position can be determined on the basis of the preliminary image data already recorded which was reconstructed having been acquired with a lower resolution, thereby improving the accuracy of reproduction of the internal structures to be imaged.

For the CT image data used in real time during CT imaging, two-dimensional image projections can be used instead of laboriously reconstructed 3D image data. The two-dimensional image projections are wholly adequate for marking a scan range and require no reconstruction time, as they can be generated directly on the basis of the scanned projection measurement data without laborious reconstruction techniques.

The use of the indefinite article "a" or "an" does not exclude the possibility of a plurality of the features in question also being present. The use of the expression "to have" does not exclude the possibility that the terms linked by the expression "to have" may be identical. For example, the computed tomography system has the computed tomography system. The use of the expression "unit" does not exclude the possibility that that the item to which the expression "unit" relates may have a plurality of components which are spatially separated from one another. In the context of the present application, the use of ordinal numbers (first, second, third, etc.) in the denotation of features serves primarily for better differentiability of the features denoted by ordinal numbers. The absence of a feature which is denoted by a combination of a given ordinal number and a term does not exclude the possibility that a feature may be present which is denoted by a combination of an ordinal number following the given ordinal number and term.

Figure 1:
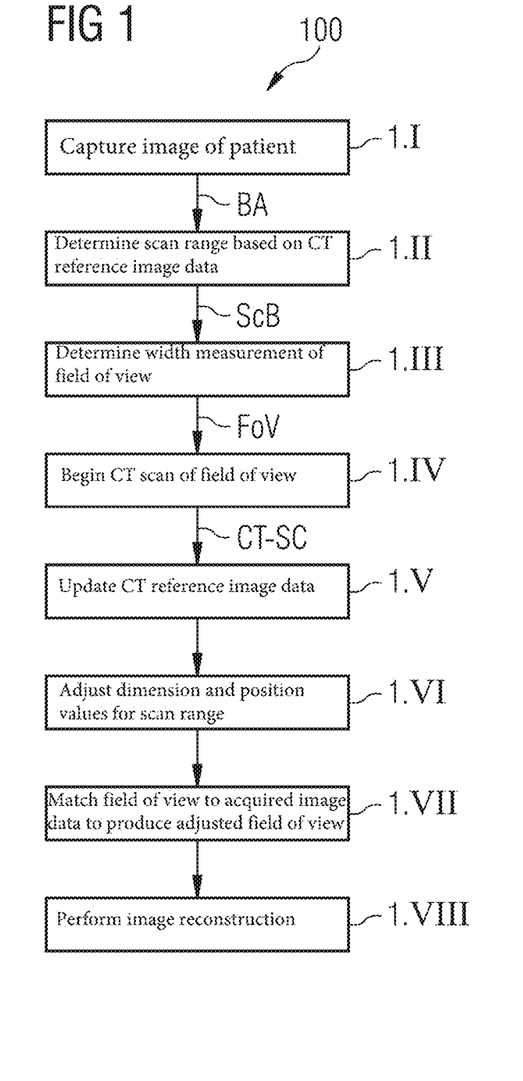
FIG. 1 shows a flow chart which illustrates a method for defining scanning parameters of a CT scan of a region of interest of an examination object using a CT system according to an example embodiment of the invention.

FIG. 1 shows a flow chart 100 illustrating an example embodiment of a method for defining scanning parameters of a CT scan of a region of interest of an examination subject using a CT system. In step 1.I, image capture BA of a patient initially takes place using a camera. The camera is disposed relative to the examination object, in this case a patient, such that at least one section of the patient which encompasses a desired field of view FoV can be recorded. In the example embodiment illustrated in FIG. 1, the camera used is a 3D camera with which a 3D profile of the patient is acquired.

In step 1.II, on the basis of the captured image BA, CT reference image data $BD_{ref}$ matching the captured image BA as closely as possible is obtained from a database. For example, the dimensions of the body region recorded on the captured image BA must match the corresponding dimensions of the reference image data $BD_{ref}$. Based on the CT reference image data $BD_{ref}$ selected, a scan range ScB is determined. That is to say, a position and a length of a region to be imaged by a subsequent CT scan in the z-direction, i.e. in the axial direction of the CT system used, is determined.

Subsequently, in step 1.III, a width measurement of a field of view FoV to be imaged is determined on the basis of the image BA captured by the camera K, so that the position as well as the dimensions of the field of view FoV to be imaged are then known.

In step 1.IV, the actual CT scan CT-SC of the determined field of view FoV is now started.

In step 1.V, the reference image data $BD_{ref}$ used for determining the scan range ScB is updated during the CT scan CT-SC. Here the already acquired CT image data BD is used for comparison in order to select matching CT reference image data $BD_{ref}$ from a database. Then, in step 1.VI, using the updated CT reference image data $BD_{ref}$, the dimension and position values for the scan range ScB are adjusted to scan range values assigned to an adjusted scan range $ScB_{adj}$. In other words, the already acquired CT image data BD is itself used to correct the scan range ScB of the CT scan CT-SC.

On completion of the CT scan CT-SC, in step 1.VII the field of view FoV, in this case the region which is to be taken into account for image reconstruction or rather image display, is correspondingly matched to the acquired image data BD so that an adjusted field of view $FoV_{adj}$ is produced. The image data BD recorded in real time during the CT scan CT-SC can, for example, in order to save time, be reconstructed with low resolution, so that the time required for image data reconstruction is matched to the real-time requirements. Finally, in step 1.VIII, the actual image reconstruction of the image data BD takes place in a resolution necessary for a subsequent diagnosis.

Figure 2:
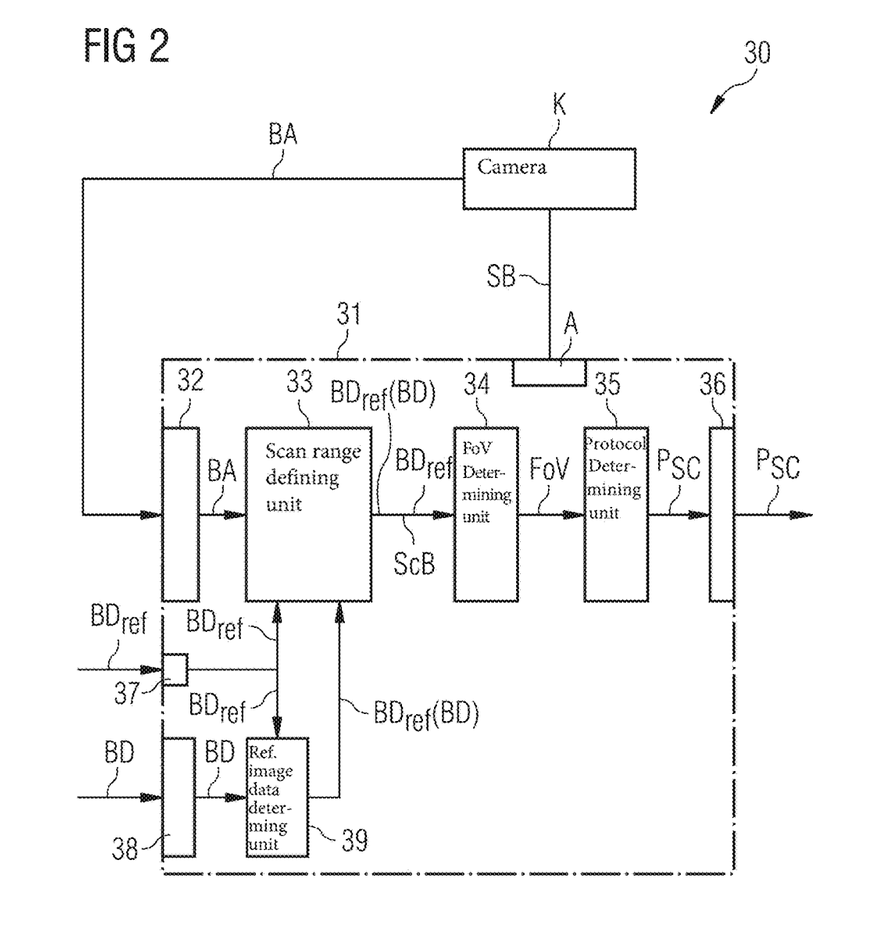
FIG. 2 shows a block diagram which illustrates a CT scan range defining device according to an example embodiment of the invention.

FIG. 2 shows a CT scan range defining device 30 for controlling a scan CT-SC of a region of interest (FoV) of a patient by a CT system. The CT scan range defining device 30 comprises a 3D camera K with which a three-dimensional image BA of at least one body section of a patient is taken prior to the start of CT imaging. The CT scan range defining device 30 additionally comprises a CT scan range defining unit 31 which processes the image BA captured by the 3D camera K. To receive the image capture data BA, the CT scan range defining unit 31 has an image capture data input interface 32. In addition, the CT scan range defining unit 31 also has a control unit A for controlling the camera K in order to trigger and control image capture BA of the examination object. Part of the CT scan range defining unit 31 is also a scan range determining unit 33.

The scan range determining unit 33 processes the received image capture data BA in the regard that the position and in particular the length of a scan range ScB in the axial direction of the CT system is determined on the basis of the image capture data BA. In addition, CT reference image data $BD_{ref}$ from a database (not shown) is received by the scan range determining unit 33 via a reference image data interface 37. The scan range determining unit 33 uses the CT reference image data $BD_{ref}$ to determine the dimensions of the scan range ScB and its position in the axial direction. Here CT reference image data $BD_{ref}$ matching the patient's dimensions determined on the basis of the image capture data BA is selected from the database.

The CT reference image data $BD_{ref}$ provides information about the position and dimensions of the patient's body structures to be imaged by the CT imaging process. Although they not been acquired directly from the patient, on the basis of the image capture BA previously performed by the 3D camera K, a corresponding CT reference image $BD_{ref}$ can nevertheless be selected from the database, the features of which image closely match the image BA captured by the 3D camera.

On the basis of the parameters determined for the scan range ScB and of the CT reference image data $BD_{ref}$, the dimensions of a field of view FoV to be imaged are then determined by a field of view determining unit 34. For example, for defining said field of view FoV, the length of the scan range ScB is used as the dimension in the z-direction, and the dimension in the width direction and depth direction, i.e. in the x- and y-direction, is determined on the basis of the CT reference image data $BD_{ref}$. In addition, a protocol determining unit 35 determines a scan protocol $P_{sc}$ of a CT imaging process, said scan protocol specifying the determined positions and dimensions (in particular the length in the z-direction) for the scan range ScB and the field of view FoV (the length corresponds to the length of the scan range, depth, width). This protocol is then output via an output interface 36 to a control unit (not shown) for controlling a scanning unit of a CT system.

The CT scan range defining unit 31 additionally comprises an image data input interface 38 which receives CT image data BD during the actual CT imaging. The CT image data BD comes from an image data reconstruction unit of a control device (see FIG. 3) of a CT system and comprises image material reconstructed in real time of the current CT imaging. That is to say, the line-by-line acquired X-ray projection measurement data is reconstructed even during the scanning process, preferably with coarse resolution, and transmitted to the CT scan range defining unit 31. In the CT scan range defining unit 31, the image data BD acquired as real time image data is transmitted to a reference image data determining unit 39 which, on the basis of the current image data BD, selects reference image data $BD_{ref}(BD)$ from the database that matches the already pictorially acquired structures of the patient undergoing the CT imaging process in respect of the dimensions and positions and the shape of the structures.

During the imaging process, this newly determined reference image data $BD_{ref}(BD)$ is used by the scan range determining unit 33 to correct the position and the dimensions of the scan range ScB. Then the selected reference image data $BD_{ref}(BD)$ is used by the field of view determining unit 34 to also correct the position and the dimensions of the field of view FoV in line with the reference image data $BD_{ref}(BD)$. In addition, during the CT imaging process the scan protocol $P_{sc}$ is modified in respect of the dimensions and positions of the scan range ScB and the field of view FoV. In this way, the CT imaging is controlled in a self-adjusting manner, thereby obviating the need to obtain a topogram prior to actual CT imaging using the CT scanning unit.

Figure 3:
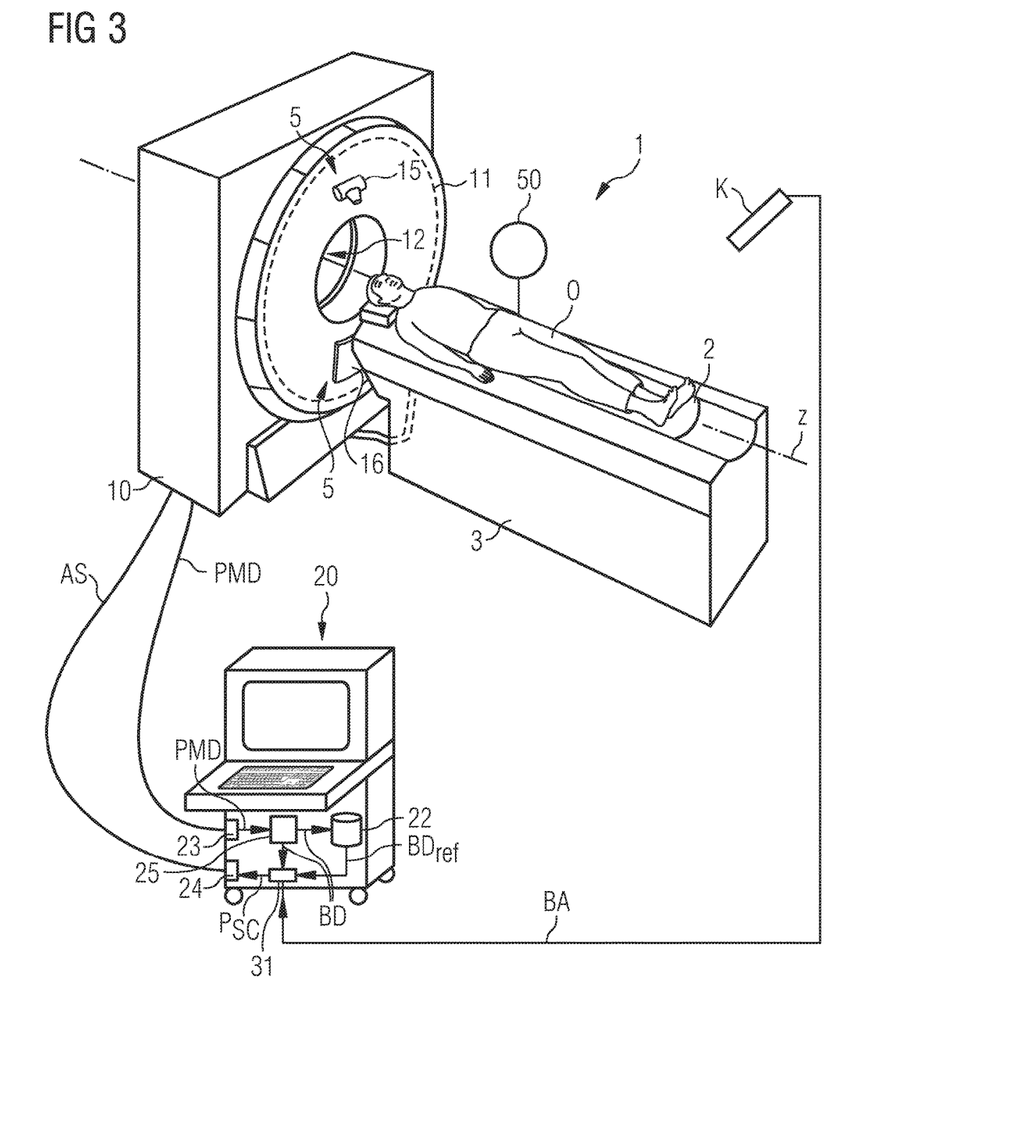
FIG. 3 shows a computed tomography system according to an example embodiment of the invention.

FIG. 3 shows a computed tomography system 1 according to an example embodiment of the invention, said system also comprising a CT scan range defining unit 31 as per the arrangement shown in FIG. 2. This CT system 1 includes a usual scanning unit 10 in which, on a gantry 11, a projection data acquisition unit 5 comprising a detector 16 and an x-ray source 15 disposed opposite said detector 16 revolves around a scanning chamber 12. Located in front of the scanning unit 10 is a patient positioning device 3, i.e. a patient table 3, the upper part 2 of which can be slid into the scanning unit 10 with a patient O positioned thereon in order to move the patient O through the scanning chamber 12 relative to the detector system 16. The scanning unit 10 and the patient table 3 are controlled by a control device 20 from which acquisition control signals AS come via a usual control interface 24 in order to control the entire system in accordance with predefined scan protocols. In the case of spiral acquisition, movement of the patient O along the z-direction, which corresponds to the system axis z passing longitudinally through the scanning chamber 12, and the simultaneous rotation of the X-ray source 15 for the X-ray source 15 relative to the patient O during scanning, produces a helical trajectory or a circular trajectory in the case of a sequential scan. The detector 16 always co-rotates with the opposite X-ray source 15 in order to acquire projection measurement data PMD which is then used for the reconstruction of volume and/or slice image data.

Likewise, a sequential scanning process can also be carried out in which a fixed position can be moved to in the z-direction and then during a revolution, a partial revolution or a plurality of revolutions the required projection measurement data PMD is acquired at the z-position in question in order to reconstruct a cross-sectional image at this z-position or to reconstruct image data BD from the projection measurement data of a plurality of z-positions. In principle, the method according to an embodiment of the invention can also be used on other CT systems, e.g. having a plurality of X-ray sources and/or detectors and/or having a detector forming a complete ring.

The projection measurement data PMD (also termed raw data in the following) acquired by the detector 16 is transferred to the control device 20 via a raw data interface 23, also termed a raw data acquisition unit. Possibly after suitable pre-processing (e.g. filtering and/or beam hardening correction), this raw data PMD is then further processed in an image reconstruction unit 25 which in this example embodiment is implemented in the control device 20 in the form of software on a processor. On the basis of the raw data PMD, said image reconstruction unit 25 reconstructs image data BD using a reconstruction technique. For example, a reconstruction technique based on filtered back-projection can be used as the reconstruction method.

The acquired image data BD is stored in a memory 22 of the control device 20 and/or displayed in the normal manner on the screen of the control device 20. It can also be fed via an interface (not shown in FIG. 3) into a network connected to the computed tomography system 1, e.g. a radiological information and image archiving system (RIS/PACS), and stored in mass storage accessible there or output as images to connected printers or filming stations. The data can thus be further processed as required and then stored or output.

The RIS is a purely administrative system for acquiring patient data and controlling the medical procedures. In addition, a Picture Archiving and Communication System (PACS) is available for long-term storage of the memory-intensive image data BD.

FIG. 3 also shows a CT scan range defining unit 31 which receives image data BA of the patient O from a camera K. On the basis of the image data BA, the CT scan range defining unit 31 determined the position and the dimensions of a scan range ScB and also defines the field of view FoV for CT imaging. As described in connection with FIGS. 1 and 2, protocol parameters for a scan protocol of the CT system 1 are also modified by the CT scan range defining unit 31 during CT imaging on the basis of the reconstructed image data BD and of reference image data $BD_{ref}$, whereby in particular the field of view FoV and the scan range ScB are matched to the situation actually to be found during the imaging CT-SC.

The CT scan range defining unit 31 is shown in FIG. 3 as part of the control device 20. In addition, the CT system 1 shown in FIG. 3 also comprises a contrast agent injection device 50 by which the patient O can be injected with a contrast agent prior to the start of a CT imaging process to enable image contrasts in a region of interest to be influenced.

Finally, it is once again pointed out that the method described above and the described CT scan range defining device 30 as well as the described computed tomography system 1 are merely preferred example embodiments of the invention and that the invention may be varied by persons skilled in the art without departing from the scope of the invention in so far as it is predefined by the claims. For the sake of completeness, it is also pointed out that the use of the indefinite article "a" or "an" does not exclude the possibility of a plurality of the features in question also being present. Likewise, the term "unit" does not exclude the possibility that the "unit" includes a plurality of components which may also possibly be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining at least one scanning parameter of a field of view of an examination object using a computed tomography (CT) system, comprising:
   performing an external image capture of external features of the examination object using an additional image capture unit to obtain an externally captured image;
   determining the at least one scanning parameter of the CT system based upon of the externally captured image; and
   performing a CT scan using the at least one determined scanning parameter, the performing the CT scan including,
   acquiring CT image data, and
   adjusting a scan range based upon the acquired CT image data.

2. The method of claim 1, wherein,
   the at least one scanning parameter includes,
   at least one of a position and at least one dimension of the scan range, and
   the performing the CT scan takes place in the determined at least one of the position and the at least one dimension of the scan range.

3. The method of claim 1, further comprising:
   determining the field of view based upon the externally captured image; and
   determining a slice of the field of view as a slice for observing a contrast agent bolus based upon the externally captured image.

4. The method of claim 1, wherein at least one of the at least one scanning parameter and the field of view is additionally determined based upon CT reference image data.

5. The method of claim 1, further comprising:
   terminating the CT scan in an automated manner based on an original scan range or the adjusted scan range.

6. The method of claim 5, wherein the terminating the CT scan further includes reducing a scanning speed of the CT scan before an end of the adjusted scan range.

7. The method of claim 6, further comprising:
   switching to another CT scanning mode having a relatively lower scanning speed before the end of the adjusted scan range.

8. The method of claim 4, wherein the determining the at least one scanning parameter further includes one of:
   using the CT reference image data, wherein the CT reference image data is selected from a database based on the examination object;
   deforming the CT reference image data to match the CT reference image data to image data recorded by the CT scan; or
   generating the CT reference image data using a statistical model based upon a totality of CT reference image data.

9. The method of claim 1, wherein the performing the CT scan further includes adjusting the scan range further based upon a machine learning method applied to the acquired CT image data.

10. The method of claim 1, wherein the adjusting the scan range includes,
registering CT reference image data used for a preliminary determination of the scan range to already acquired CT image data,
scanning at least one CT image slice, and
selecting new CT reference image data based on the acquired CT image data from a database in an automated manner after the scanning the at least one new CT image slice.

11. The method of claim 1, further comprising:
adjusting the field of view upon completion of the performing of the CT scan based upon the acquired CT image data.

12. A non-transitory computer program product comprising a computer program, directly loadable into a storage device of a computed tomography system, including program sections to carry out the method of claim 1 when the computer program is executed in the computed tomography system.

13. A non-transitory computer readable medium, storing program sections readable and executable by a processor, to carry out the method of claim 1 when the program sections are executed by the processor.

14. The method of claim 1, further comprising:
determining a slice of the field of view as a slice for observing a contrast agent bolus based upon the externally captured image.

15. The method of claim 1, wherein the adjusting the scan range further includes reducing a scanning speed for the CT scan before an end of the adjusted scan range.

16. The method of claim 2, further comprising:
adjusting the field of view upon completion of the performing of the CT scan based upon the acquired CT image data.

17. The method of claim 1, further comprising:
adjusting the field of view based upon the acquired CT image data.

18. A non-transitory computer program product comprising a computer program, directly loadable into a storage device of a computed tomography system, including program sections to carry out the method of claim 2 when the computer program is executed in the computed tomography system.

19. A non-transitory computer readable medium, storing program sections readable and executable by a processor, to carry out the method of claim 2 when the program sections are executed by the processor.

20. The method of claim 1, wherein,
the at least one scanning parameter is a scanning parameter for modulating an x-ray dose, and
the performing of the CT scan includes modulating the x-ray dose as a function of the at least one determined scanning parameter.

21. The method of claim 1, wherein the adjusting the scan range further includes,
acquiring low-resolution provisional image data in real time, and
determining position and dimensions of internal structures of the examination object to be imaged based upon the low-resolution provisional image data.

22. A computed tomography (CT) scanning parameter device, comprising:
processing circuitry configured to,
control an external image capture unit, the external image capture unit configured to capture an externally captured image of an examination object,
determine at least one scanning parameter of a CT system based upon the externally captured image, and
adjust a scan range based upon acquired CT image data.

23. A computed tomography (CT) system, comprising:
a scanning unit configured to acquire a region of interest of an examination object;
an external image capture unit configured to capture an externally captured image of the examination object; and
processing circuitry configured to
control the scanning unit,
control the external image capture unit,
determine at least one scanning parameter of the CT system based upon the externally captured image, and
adjust a scan range based upon acquired CT image data.

* * * * *